United States Patent

Laudadio

[11] Patent Number: 5,931,793
[45] Date of Patent: Aug. 3, 1999

[54] METHOD OF DETECTING NEUROPATHY BY VIBRATION

[76] Inventor: Charles Laudadio, 227 William Penn Blvd., West Chester, Pa. 19382-8432

[21] Appl. No.: 08/866,214

[22] Filed: May 30, 1997

Related U.S. Application Data

[60] Provisional application No. 60/019,164, Jun. 5, 1996.
[51] Int. Cl.⁶ ....................................................... A61B 5/05
[52] U.S. Cl. ............................................................ 600/552
[58] Field of Search .................................. 600/552, 553, 600/557, 587

[56] References Cited

U.S. PATENT DOCUMENTS

| | | | |
|---|---|---|---|
| 2,704,539 | 3/1955 | Fisher | 600/557 |
| 4,881,526 | 11/1989 | Johnson et al. | 128/24.5 |
| 5,433,211 | 7/1995 | Brammer et al. | 600/552 |
| 5,458,119 | 10/1995 | Vanharanta | 600/557 |

*Primary Examiner*—Cary O'Connor
*Assistant Examiner*—Pamela L. Wingood
*Attorney, Agent, or Firm*—Connolly & Hutz

[57] ABSTRACT

A vibration pocket device is utilized for detecting severe neuropathy. The device is generally the size and shape of a conventional pen and includes a stimulus head or probe mounted at an end of the device. The head or probe is caused to vibrate and is applied to a patient's extremity in order to determine if the patient can feel the vibration.

6 Claims, 1 Drawing Sheet

METHOD OF DETECTING NEUROPATHY BY VIBRATION

CROSS-REFERENCE TO RELATED APPLICATIONS

This application is based upon provisional application Ser. No. 60/019,164 filed Jun. 5, 1996.

BACKGROUND OF THE INVENTION

Vibration testing has long existed in various manners. For example, vibration threshold testing devices are currently being used which include two fixed probes in one or two boxes which are placed on a table or floor. The patient must touch them with the fingers or toes and tell which is vibrating. A further vibrating tool known as a Biothesiometer which is similar to vibrating devices sold in adult paraphernalia shops is applied to the extremity and the vibration level is turned up until the patient can feel the vibration. The level is then read off a meter. The above types of devices have also been computer driven. A further type of vibration testing is by the utilization of a tuning fork which can be applied to the extremity.

The use of a vibrating pen is also known but not for detecting nerve impairment (neuropathy). For example, a silent call from a vibrating pen marketed by Solarwide Inc. sends a signal to indicate that the user has a call on a cellular phone. Another form of vibrating pen known as a Wiggle Writer for children operates on a similar principle using an offset motor which causes the pen tip to draw circles. See, for example, U.S. Pat. No. 5,208,987.

SUMMARY OF THE INVENTION

An object of this invention is to provide a method and device for detecting nerve impairment or neuropathy.

A further object of this invention is to provide such a method which may utilize a vibration pocket device similar to a vibrating pen so that the device may be inexpensively made and conveniently operated.

In accordance with one embodiment of this invention the vibration pocket device includes a battery operated vibrating head having, for example, a piezoelectric transducer so that the head rapidly vibrates axially at a fixed magnitude. The vibrating head is applied against the patient's extremity to determine if the patient can feel the vibration.

In an alternative embodiment the vibration pocket device is of the offset motor type wherein instead of a writing tip the device includes a probe which would vibrate and be placed against the patient's extremity.

THE DRAWINGS

FIG. 1 is a schematic cross-sectional view in elevation of a vibration pocket device which may be used in accordance with one embodiment of this invention; and FIG. 2 is a schematic cross-sectional view in elevation of an alternative vibration pocket device which may be used in accordance with this invention.

DETAILED DESCRIPTION

Figure 1:
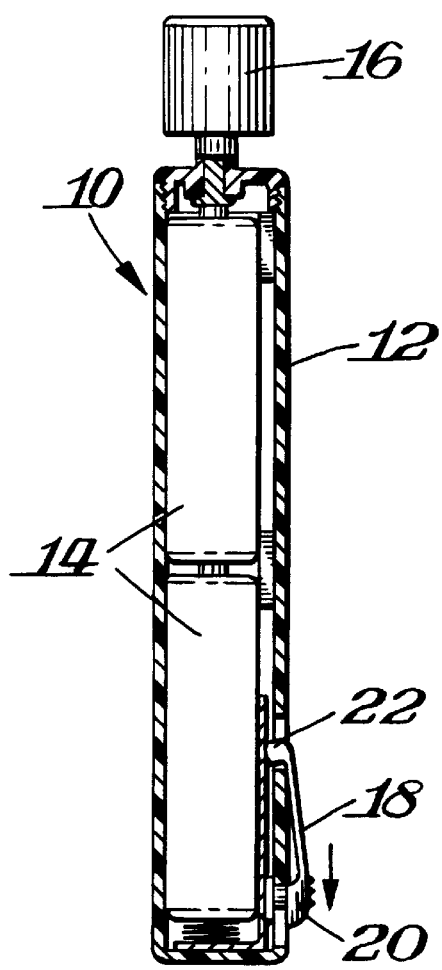

FIG. 1 illustrates a vibration pocket device 10 in accordance with this invention. As shown therein device 10 includes an outer case 12 which is used for housing a pair of batteries 14. The end of the case includes a vibrating head 16 having a vibration device powered by the batteries. The vibration device may, for example, by a piezoelectric transducer which preferably vibrates in such a manner that the vibration can not be heard but a vibration frequency of about 100–300 Hz (preferably about 125–200 Hz) has a high enough pulsation to be felt.

As also shown in FIG. 1 a spring clip 18 is mounted near the end of case 12 remote from the vibrating head 16. Clip 18 is generally similar to conventional clips used with pens for holding a pen in place in, for example, a user's pocket. Thus, spring clip 18 includes an end 20 rigidly or slidably anchored to case 12 and a free end 22 having an inward projection which is resiliently biased toward case 12 but may be moved away from the case to permit the clip to be hooked onto the user's pocket. Preferably, case 12 has an opening through which end 22 may extend so that end 22 when penetrating the opening makes electrical contact within case 12 to act as an on switch or actuator for the vibration device. When the vibration device 10 is mounted in the pocket, the interposition of fabric from the user's pocket prevents contact by the actuating portion 22 of clip 18 so that the vibration device is in an off position.

As illustrated, clip 10 may be slidably mounted on the outer surface of case 12 so as to selectively dispose the actuating end 22 either within the opening in the wall of case 12 or to a second position where the actuating end abuts against the wall itself rather than penetrating through any opening. Thus, device 10 would be in an on condition when the clip is slid to permit actuating member 22 to penetrate through the case wall or would be in an off position when the clip is slid so that the actuating member 22 is against the outer surface of the wall.

Where clip 18 is slidably mounted actuating member 22 could be slidably moved to three different actuating conditions where it would slidably actuate three different switch positions for the transducer to select a pressure amplitude of vibration of low, medium and high for probe 16.

Figure 2:
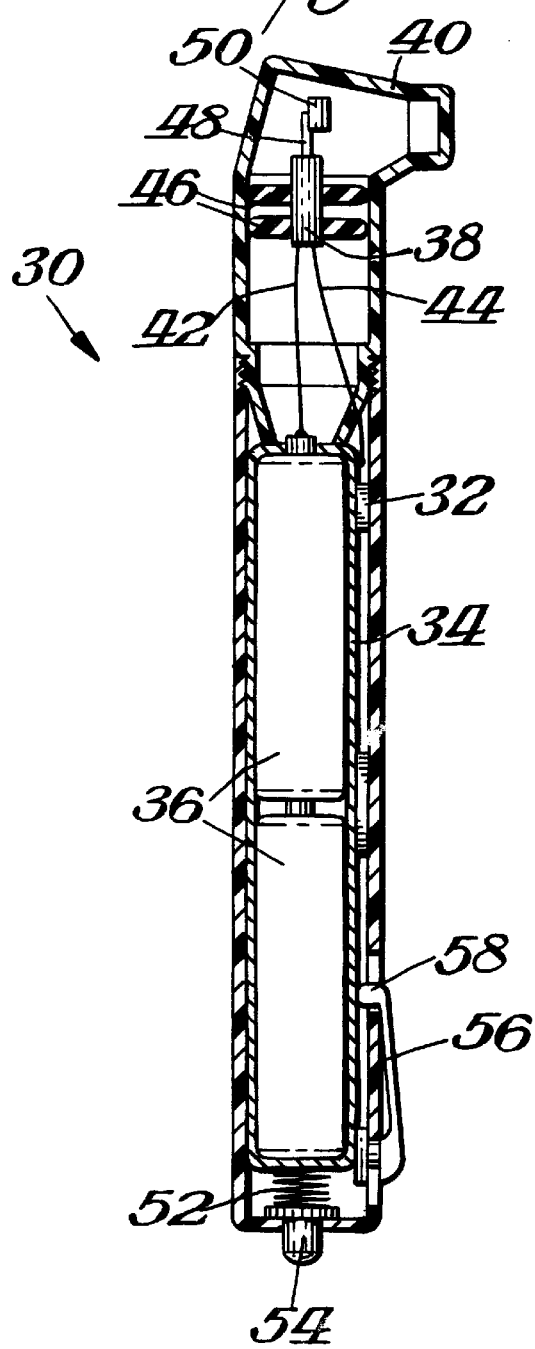

FIG. 2 shows an alternative form of vibration pocket device 30 which would be constructed along the principles of a vibrating pen having an offset motor. Such device 30 operates similar to the device of U.S. Pat. No. 5,208,987, the details of which are incorporated herein by reference thereto. As shown in FIG. 2 device 30 includes an outer case 32 and an inner case 34 made of an electrically conductive material in which is mounted a pair of batteries 36. A small DC motor 38 is mounted in the stimulus head 40 at one end of device 30. An electrical wire 42 electrically connects the motor 38 with batteries 36 while a second electrical wire 44 connects the motor 38 with the conductive inside case 34. Motor 38 is mounted in place in a stable manner by isolating grommets 46.

Motor 38 includes a shaft 48 to which is mounted an offset weight 50. Thus, when shaft 48 rotates about its axis weight 50 rotates along a closed arc causing a vibration. A spring 52 is mounted at the vibrating end of the device 30 against a probe 54 extending out of the vibrating end of case 32.

In operation of the device 30 of FIG. 2 the offset motor creates vibration which is transmitted to probe 54. Probe 54 can be flat, curved, beveled, straight or any other configuration which would be suitable to apply against the skin. Preferably, as with case 12, case 32 can be an outer plastic or non-conductive material with an inner tube 34 made of metal or having a metallic conducting coating to conduct the electricity to one lead of the motor through wire 44. The positive end of a battery 36 comes in contact with the other lead of the motor 38 through wire 42. The rubber or plastic grommets isolate the motor from the housing while also stably securing the motor in place.

As also shown in FIG. 2 a clip 56 may be mounted on case 32 similar to clip 18. Clip 56 would thus include an actuating arm 58 which could extend through outside case 32 into selective contact with inner conducting case 34 for switching on the motor. Clip 56 may be similar to clip 18 by being slidably mounted and, if desired, by being movable to low, medium and high amplitude vibration positions.

It is to be understood that the use of a clip to selectively actuate device 10 or device 30 is a preferred practice of the invention, but other on/off switches could be used which do not have the added function of being able to mount the device in a user's pocket.

In operation with either device 10 or device 30 the device would be used as a diagnostic medical device to detect peripheral neuropathy. The invention is based upon the principle of creating a vibration by a small portable device shaped like a pen that preferably can be clipped in the shirt pocket. The vibrating head or probe of the pen is applied to the patient's extremity (finger, toe, face, etc.) and vibrates at a fixed magnitude which will determine a specific level or threshold of the patient's ability to detect vibration. The magnitude, although fixed, can be selected to be low (for minimal detection of threshold impairment), medium (to detect moderate neuropathy) or high (to detect severe neuropathy). If the patient can feel the vibration, set at a preselected level, the patient's threshold is lower than the level set. Conversely, if the patient cannot feel the vibration, then the patient's threshold is higher than the level set.

The device 10 or 30 can be made of any suitable materials. The outer case 12 or 32 can be plastic or metal of any color. The case can contain an outer barrel or a barrel within a barrel to isolate the vibration from the outer case. The batteries would preferably be mounted inside a conducting aluminum plated cardboard barrel which in turn is mounted inside the outer case or housing barrels to provide a complete electrical circuit between the switch batteries and motor or can be placed directly in the casing and wiring can be used to complete the circuit.

The vibrating tip can be plastic or metal and can be tubular or solid projecting out of one end of the pen or such as in FIG. 2 or can be the whole head of the pen such as in FIG. 1.

The vibration can be produced by the use of a small DC motor with an offset weight on the shaft, such as in FIG. 2 or by a piezoelectric or other transducer providing that the frequency is low enough not to be heard by the patient and the amplitude of vibration is sufficient to allow detection.

The switch can be a clip as illustrated in FIGS. 1–2 or a button on top or on the side of the device.

Use of such a vibration pocket device in the methods of this invention greatly facilitates performing a quick, but accurate test of vibration threshold since the stimulus will be of a predetermined level of vibration as compared to the tuning fork and the test would be very simply and fast.

The device, itself could be made for a few dollars so that it can be provided to many physicians and nurses who treat patient's at risk of neuropathy (e.g. diabetics) to allow them to obtain a quick assessment on their patients. The portability and ease of testing would facilitate this quick screening. Where patients are found who can not feel the vibration the patients would be referred for more detailed testing.

Although vibratory testing devices have been around for some time and although vibrating pens are known, the present invention represents the first time that a medical device has been used that tests for vibration perception threshold utilizing a pen like device for the electronic tester. The unobviousness of the invention is apparent when considering that billions of dollars are spent each year on diabetic foot problems related to diabetic neuropathy. Yet a device such as with the invention has not been used. However, if a simple, inexpensive device such as with this invention were available to nurses and physicians, neuropathy could be detected early and many ulcers, infections, and amputations might be avoided by instituting proper foot care early.

What is claimed is:

1. In a method for detecting peripheral neuropathy comprising providing a pen-like vibration device having a vibratable probe, actuating the probe, applying the vibrating probe against the skin of the user with the probe vibrating at a predetermined magnitude, determining the threshold of patient's ability to detect vibration by the threshold being lower than the predetermined magnitude when the patient can feel the vibration and the threshold being higher than the predetermined magnitude when the patient cannot feel the vibration, the vibration device including an elongated case with a spring clip for holding the device in a pocket by interposing fabric from the pocket between the spring clip and the case, actuating the probe by contacting an electrically conductive surface in the case with the spring clip, and inactivating the probe when an electrically non-conductive material is interposed between the electrically conductive surface and the spring clip.

2. The method of claim 1 wherein the probe is applied against an extremity of the patient.

3. The method of claim 1 including interposing the electrically non-conductive material by sliding the clip to a position in contact with an electrically non-conductive portion of the casing.

4. The method of claim 1 wherein the threshold of magnitude includes a low threshold for detecting minimal threshold impairment and a medium threshold for detecting moderate neuropathy and a high threshold for detecting severe neuropathy.

5. The method of claim 1 wherein the probe is a vibrating head extending coaxially from a casing, and vibrating the head by a piezoelectric transducer.

6. The method of claim 1 wherein the probe extends from one end of a casing having a motor at the other end of the casing with a weight mounted offset from the shaft of the motor, and actuating the motor to rotate the offset weight to cause vibration of the probe.

\* \* \* \* \*